(12) United States Patent
Kantner

(10) Patent No.: US 8,968,772 B2
(45) Date of Patent: Mar. 3, 2015

(54) WATER-SOLUBLE PRESSURE SENSITIVE ADHESIVES

(71) Applicant: 3M Innovative Properties Company, St. Paul, MN (US)

(72) Inventor: Steven S. Kantner, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/753,958

(22) Filed: Jan. 30, 2013

(65) Prior Publication Data

US 2013/0143991 A1 Jun. 6, 2013

Related U.S. Application Data

(63) Continuation of application No. 12/766,505, filed on Apr. 23, 2010, now abandoned.

(60) Provisional application No. 61/173,307, filed on Apr. 28, 2009.

(51) Int. Cl.

| | |
|---|---|
| A61L 15/16 | (2006.01) |
| A61F 15/00 | (2006.01) |
| A61F 13/20 | (2006.01) |
| C07C 67/08 | (2006.01) |
| C09J 177/00 | (2006.01) |
| A61F 13/02 | (2006.01) |
| A61L 15/58 | (2006.01) |
| C08F 220/34 | (2006.01) |
| C09J 133/14 | (2006.01) |
| C09J 139/06 | (2006.01) |
| A61F 13/00 | (2006.01) |

(52) U.S. Cl.
CPC ............ *C09J 177/00* (2013.01); *A61F 13/023* (2013.01); *A61L 15/585* (2013.01); *C08F 220/34* (2013.01); *C09J 133/14* (2013.01); *C09J 139/06* (2013.01); *A61F 2013/00642* (2013.01); *A61F 2013/00646* (2013.01); *A61F 2013/00659* (2013.01); *A61F 2013/00868* (2013.01)
USPC ........ 424/448; 602/54; 604/385.05; 524/386; 524/376; 524/310; 524/317

(58) Field of Classification Search
None
See application file for complete search history.

(56) References Cited

U.S. PATENT DOCUMENTS

| | | | |
|---|---|---|---|
| 3,238,100 A | 3/1966 | Meyer | |
| 3,969,498 A | 7/1976 | Catania | |
| 4,324,595 A | 4/1982 | Kasprzak | |
| 4,331,576 A | 5/1982 | Colon | |
| 4,393,048 A | 7/1983 | Mason, Jr. | |
| 4,521,404 A | 6/1985 | Lorenz | |
| 4,750,482 A | 6/1988 | Sieverding | |
| 4,990,339 A | 2/1991 | Scholl | |
| 5,182,323 A | 1/1993 | Russell | |
| 5,276,079 A | 1/1994 | Duan et al. | |
| 5,614,310 A | 3/1997 | Delgado | |
| 5,637,296 A | 6/1997 | Rocafort | |
| 5,688,523 A | 11/1997 | Garbe | |
| 5,735,812 A | 4/1998 | Hardy | |
| 5,780,047 A | 7/1998 | Kamiya | |
| 6,019,997 A | 2/2000 | Scholz | |
| 6,121,508 A | 9/2000 | Bischof | |
| 6,136,866 A | 10/2000 | Himmelsbach | |
| 6,159,498 A | 12/2000 | Tapolsky | |
| 6,169,224 B1 | 1/2001 | Heinecke | |
| 6,171,985 B1 | 1/2001 | Joseph | |
| 6,191,221 B1 | 2/2001 | McAmish | |
| 6,270,783 B1 | 8/2001 | Slavtcheff | |
| 6,576,575 B1 | 6/2003 | Griesbach, III | |
| 6,576,712 B2 | 6/2003 | Feldstein | |
| 7,078,582 B2 | 7/2006 | Stebbings | |
| 2002/0037977 A1 | 3/2002 | Feldstein | |
| 2002/0187181 A1 | 12/2002 | Godbey | |
| 2003/0170308 A1 | 9/2003 | Cleary | |
| 2004/0247655 A1 | 12/2004 | Asmus | |
| 2005/0238703 A1 | 10/2005 | Inosaka | |
| 2006/0263322 A1 | 11/2006 | Konno | |
| 2007/0082036 A1 | 4/2007 | Dixon | |

FOREIGN PATENT DOCUMENTS

| | | |
|---|---|---|
| EP | 0896993 A1 | 2/1999 |
| JP | 63-150363 A | 6/1988 |
| JP | 2000-212074 | 2/2000 |
| JP | 2003-160774 A | 6/2003 |
| JP | 2005-89438 A | 4/2005 |
| WO | WO 95/05416 | 2/1995 |
| WO | WO 02/04570 | 1/2002 |

OTHER PUBLICATIONS

Chu, "Viscoelastic Properties of Pressure Sensitive Adhesives", Chapter 8, Handbook of Pressure Sensitive Adhesive Technology, Donatas Satas, 2$^{nd}$ Edition, Van Nostrand Reinhold, pp. 158, 172, 173, (1989).
Satas, "Hospital and First Aid Products", Chapter 25, Handbook of Pressure Sensitive Adhesive Technology, Donatas Satas, Second Edition, Van Nostrand Reinhold, pp. 627-642, (1989).
Schlossman, The Chemistry and Manufacture of Cosmetics, vol. I—Basic Science, Third Edition, Allured Publishing Corp., (2000).
Search Report of PCTUS2010-032230, 4 pages, dated Dec. 30, 2010.

*Primary Examiner* — Jeffrey T Palenik
(74) *Attorney, Agent, or Firm* — Kevin W. Weber

(57) ABSTRACT

A water-soluble pressure sensitive adhesive comprises a homogeneous blend comprising (a) a polymer selected from the group consisting of N-vinyl caprolactam homopolymers, N-vinyl pyrrolidone copolymers, and mixtures thereof and (b) a non-volatile plasticizer comprising a monohydric or polyhydric alcohol having hydrophilic-lipophilic balance of about 2 to about 10. The N-vinyl pyrrolidone copolymers comprise about 60% or less by weight N-vinyl pyrrolidone.

19 Claims, No Drawings

WATER-SOLUBLE PRESSURE SENSITIVE ADHESIVES

CROSS REFERENCE TO RELATED APPLICATIONS

This application is a continuation of application Ser. No. 12/766,505 filed Apr. 23, 2010, which claims priority to Provisional Application No. 61/173,307, filed Apr. 28, 2009, the disclosures of which is incorporated by reference in their entirety herein.

FIELD

This invention relates to water-soluble pressure sensitive adhesives that are useful, for example in medical tape, bandage, wound dressing, and patch constructions.

BACKGROUND

Removing a bandage adhered to the skin can be very painful. In addition, people with fragile or delicate skin or with chronic wounds that require repeated applications of dressings are often concerned about skin stripping and other damage.

The conflicting requirements of high adhesion to skin so that a bandage stays secure and gentle removal so that skin is not stripped, hair is not pulled, and residue is not left behind has been approached in various ways. These approaches include, for example, increasing the breathability of the adhesive to maintain good skin integrity for lower removal trauma (see, for example, U.S. Pat. No. 5,614,310), "stretch release" technology (see, for example, U.S. Pat. No. 7,078,582), reinforcing the skin with a film forming polymer prior to applying the bandage (see, for example, U.S. Pat. No. 4,324,595), and migrating a debonding agent like body lotion or hexamethyl disiloxane through a porous backing to the skin/adhesive interface (see, for example, U.S. Pat. No. 6,136,866). Many of these approaches compromise in-use adhesion, however, and others require an extra step.

Because of theses drawbacks, there has been interest in using water-soluble pressure sensitive adhesives (PSAs) to make hurt-free bandages that readily dissolve off in water. Unfortunately, most water-soluble PSAs pick up moisture, which reduces their cohesive strength. Water-soluble patches comprising a water-soluble adhesive and water-soluble backing for delivery of an active ingredient are described in U.S. Patent Application Pub. No. 2002/0187181. These patches, for example, need to be manufactured under low humidity conditions and packaged individually in foil packaging to prevent excess uptake of moisture in humid environments.

SUMMARY

In view of the foregoing, we recognize that there is a need in the art for adhesives for use in bandages that eliminate concerns around the removal of the bandages (for example, pain, skin stripping, and residue) by providing removal by dissolution. We further recognize that it would be advantageous for such adhesives to be less hygroscopic than currently available water-soluble adhesives so that the bandages can be compatible with conventional packaging and be more suitable for long term wear.

Briefly, in one aspect, the present invention provides a water-soluble pressure sensitive adhesive (PSA). The PSA comprises a homogeneous blend comprising (a) a polymer selected from the group consisting of N-vinyl caprolactam homopolymers, N-vinyl pyrrolidone copolymers, and mixtures thereof and (b) a non-volatile plasticizer comprising a monohydric or polyhydric alcohol having hydrophilic-lipophilic balance of about 2 to about 10. The N-vinyl pyrrolidone copolymers comprise about 60% or less by weight N-vinyl pyrrolidone.

As used herein, "water-soluble" means that a material so described can be dissolved in a 10-fold excess of water within about 2 minutes with only gentle agitation required; "pressure sensitive adhesive" or "PSA" means a normally tacky adhesive that adheres with gentle pressure (for example, finger pressure); "homogenous" means that the PSA has a substantially homogeneous appearance to the naked eye (that is, the liquid phase is compatible with the polymer and essentially no phase separation can be observed with the naked eye; and "non-volatile" means having vapor pressures below about 1.0 mm Hg at 20° C. (preferably, below about 0.5 mm Hg at 20° C.; more preferably, below about 0.3 mm Hg at 20° C.; most preferably, below about 0.1 mm Hg at 20° C.).

The PSAs of the invention are readily water-soluble and they surprisingly also have low hygroscopicity. For example, the PSAs of the invention increase in weight less than about 15% after two days at 75% relative humidity and 40° C. (preferably, less than about 10% after two days at 75% relative humidity and 40° C.) without compromising cohesive strength.

In another aspect, the present invention provides devices for skin contacting applications (for example, tapes, bandages, wound dressings, or patches) comprising a flexible backing and a water-soluble PSA of the invention. In some embodiments, the devices of the invention further comprise a water-soluble backing and optionally a water-soluble pad. Thus, the entire device can be easily dissolved off the skin with water.

DETAILED DESCRIPTION

The present invention comprises a homogenous blend of a polymer with a plasticizer which when applied to a backing provides a PSA film thereon which is water-soluble.

Polymer

The PSAs of the invention comprise a polymer selected from the group consisting of N-vinyl caprolactam (NVC) homopolymers, N-vinyl pyrrolidone (NVP) copolymers, and mixtures thereof. The NVP copolymers comprise about 60% or less by weight NVP (preferably, about 50% or less; more preferably, about 40% or less; most preferably, about 30% or less).

Examples of useful NVP copolymers include NVC/NVP copolymers and vinyl acetate (VOAc)/NVP copolymers. The VOAc/NVP copolymers typically contain about 20% by weight or more NVP. NVC homopolymers and such NVP copolymers provide water solubility and adhesive properties without having excessive hygroscopicity.

A preferred polymer is a copolymer of N-vinyl pyrrolidone and vinyl acetate comprising from about 30% to about 50% by weight N-vinyl pyrrolidone.

Optionally, low levels of comonomers may be present in amounts of up to about 10% by weight provided that they do not contain carboxylic acid functionality or tetraalkyl ammonium functionality.

Polymers suitable for use in the PSAs of the invention may be an uncrosslinked polymer or mixture of polymers with an overall number average molecular weight between about 10,000 and about 100,000 daltons. Such polymers provide a good balance of cohesive strength and water solubility.

Useful commercially available copolymers and homopolymers are marketed by ISP Corp. (Wayne, N.J., United States) under the trade names Gaffix™ VC-713, Advantage™ HC-37, Advantage™ LC-A, Aquaflex™ SF-40, and PVP/VA E-335, I-335, E-535, I-535, E-635, W-635, and by BASF of Germany under the trade names Luviskol™ VA 37 E, 37 I, 55 I, 64 W, 64 P, and Luviskol™ Plus. The NVC/NVP copolymers in these commercial products contain small amounts of tertiary amine comonomers as disclosed in U.S. Pat. Nos. 5,637,296 and 4,521,404.

Typically the total polymer content will range from about 35% to about 75% by weight of the PSA formulation. Adhesive compositions containing this level of polymeric matrix have a desirable balance of tack, softness, adhesiveness, and cohesive strength.

Plasticizers

The PSAs of the invention also comprise a non-volatile plasticizer. Suitable plasticizers include, but are not limited to, monohydric alcohols and polyhydric alcohols with a hydrophilicity expressed by having a calculated hydrophilic-lipophilic balance (HLB) in the range of about 2 to about 10 (preferably in the range of about 3 to about 9.5; most preferably in the range of about 4 to about 9). Such materials are weak hydrophiles and in many cases have low water solubility. The HLB system was originally developed as a means of classifying surface active agents, particularly non-ionic surfactants. It has broader application in characterizing compounds that have hydrophilic and hydrophobic parts that are too small to spontaneously aggregate into micelles, such as hydrotropes. As used herein, the utility of a given plasticizer is based on the HLB calculated for it using the group contribution method developed by Davies.

The non-volatile plasticizers have vapor pressures below about 1.0 mm Hg at 20° C. (preferably, below about 0.5 mm Hg at 20° C.; more preferably, below about 0.3 mm Hg at 20° C.; most preferably, below about 0.1 mm Hg at 20° C.).

In some embodiments, the water solubility of the plasticizer may be less than about 10 g/100 g (preferably, less than about 5 g/100 g). Plasticizers that are completely miscible with water in all proportions are also useful.

Classes of materials useful as plasticizers in the PSA include polyether polyols where the carbon to oxygen mole ratio is greater than about 2.5 to 1, polyester polyols, C5-C10 alkyl diols, C4-C10 carboxylate monoesters of propylene glycol, C4 to C10 carboxylate mono- and diesters of glycerin, C4-C10 alkyl monoethers of propylene glycol, C4 to C10 alkyl mono- and diethers of glycerin, C4-C10 alkyl esters of lactic acid, C2-C4 triesters of citric acid, and the like, and mixtures thereof.

Examples of useful polyether polyols include the poly (alkylene oxide) glycols wherein the alkylene unit has 2 to 6 carbon atoms, such as poly(1,2-propylene oxide) glycol, poly (1,3-propylene oxide) glycol, poly(tetramethylene oxide) glycol, poly(pentamethylene oxide) glycol, poly(hexamethylene oxide) glycol and poly (1,2-butylene oxide) glycol; random or block copolymers of ethylene oxide and 1,2-propylene oxide (used in proportions such that the carbon to oxygen mole ratio in the glycol exceeds about 2.5:1) and poly-formals prepared by reacting formaldehyde with glycols such as pentamethylene glycol, or mixtures of glycols, such as a mixture of tetramethylene and pentamethylene glycols. Mono or dialkyl ethers and esters of such polyols are also useful as are branched polyols.

Both liquid and solid non-volatile plasticizers can be used in the PSAs of the present invention.

Typically, the plasticizer will comprise from about 10% to about 75% by weight of the PSA.

Optional Components

The water-soluble PSAs of the invention can optionally comprise additives including one or more active agents as detailed below, or low levels of compatible anionic, cationic, nonionic or amphoteric surfactant(s). The use of such surfactants can improve the adhesion of the PSA to oily surfaces by providing the PSA lipophilic properties as reported, for example, in U.S. Pat. No. 6,121,508. The compatibility between the PSA and the oily surface is improved by incorporating the surfactants into the PSA. The surfactant also may serve to make hydrophobic active ingredients more compatible with the PSA. Addition of tackifiers, antioxidants, fillers, and the like to the PSA is also within the scope of the present invention.

Devices for Skin Contacting Applications

PSAs that stick to skin are widely used in medical and athletic skin contacting applications, offering the best, if not the only, means for short term secural of various devices to the human body. As detailed in Chapter 25, Hospital and First Aid Products, by Donatas Satas and A. Maria Satas, in Handbook of Pressure Sensitive Adhesive Technology, Second Edition, D. Satas, Ed., 1989, PSAs are used for immobilization and dressing or intravenous (IV) line secural, to adhere surgical drapes and protective padding, and in devices which deliver drugs transdermally or sense electrocardiograms. The role of these PSAs may be solely adhesion, such as in tapes and bandages, or it may also provide a benefit beyond adhesion, such as serving as a reservoir for active ingredients delivered to or through the skin. The water-soluble PSAs of the present invention are particularly suited for use in tapes, bandages, and patches for delivery of active ingredients.

Devices of the invention can be removed gently and substantially without pain by dissolving (for example, soaking) the water-soluble PSA in cold or warm water. In addition, the PSA is not very hygroscopic making the devices suitable for long term wear. They are also more compatible with conventional packing (that is, they don't require individual foil packaging).

Backing

When provided as a tape, dressing, bandage, or patch, the PSA is typically provided on a thin, flexible backing using methods known in the art. Useful backings include nonwoven fibrous webs, woven fibrous webs, knits, foams, films and the like. It is also preferred, but not required, that the backing be at least partially permeable to moisture vapor released through a patient's skin. For example, it can be preferable that the backing has a moisture vapor transmission rate of about 500 g/m$^2$/24 hours. In some instances, permeability can be obtained and/or increased by providing a number of openings in the backing. Such openings also provide access for aqueous solutions to dissolve the water-soluble PSA, making the removal of, for instance, a bandage quicker and more uniform than when aqueous penetration occurs only from the edge. Openings are inherent in woven, knit, and non-woven backings and may be provided in film backings by generating apertures or perforations using mechanical or thermal means.

Other examples of useful backings include water-soluble films and fabrics. These backings can be generated from any of the known natural or synthetic water-soluble or water-dispersible film-forming polymers and oligomers. In certain embodiments, the backing is selected to be cold water-soluble. Suitable polymers and oligomers include, but are not limited to, vegetable natural polymers such as alginic acid and alginic acid derivatized polymers, arabinogalactan, cellulose derivatives including but not limited to hydroxyethyl and hydroxypropyl cellulose, starch and starch derivatives; microorganism-derived natural polymers such as polysaccharides, polymers derived from animals including gelatin, collagen, mucopolysaccharides and the like; polyoxyalkylenes; polymers and copolymers derived from ethenically unsaturated monomers including, but not limited to, vinylic monomers, acrylates and methacrylates, acrylamides and methacrylamides, and the like; polyethyleneimines; and mixtures including one or more of the foregoing. Polymers of polyvinyl alcohols, polyvinyl pyrrolidone, proteins such as gelatin and collagen and derivatives thereof, or carbohydrates such as arabinogalactan have been recognized as having particular utility. Water-soluble polyvinyl alcohol films are commercially available from Aicello Chemical Company, Toyohashi, Japan under the tradename Solublon and from Monosol LLC in Merrillville, Ind.

Polymers of polyvinyl alcohols may be prepared from polyvinyl acetate and can be commercially obtained in a variety of molecular weights and hydrolysis levels. The hydrolysis level determines, in part, whether the polymer is cold water-soluble or warm water-soluble, with hydrolysis greater than about 87% resulting in more crystalline polymers, thereby requiring higher temperatures to dissolve the polymer. The speed at which the polymer dissolves is determined, in part, by the molecular weight of the polymer and the presence of additional additives such as plasticizers or crosslinkers. Certain plasticized polyvinyl alcohol resins are thermoplastic and may be melt extruded or cast into films.

Plasticizers can be used to reduce the brittleness of the water-soluble backing, thereby making it tougher, more conformable and generally improving its handling properties. Using water alone as the plasticizer yields a backing that is prone to rapid loss of moisture and a concomitant change into a glassy or brittle material when exposed to ambient conditions. Hence suitable plasticizers generally include alcohols, mixtures of alcohols, and mixtures of water and alcohols. Suitable plasticizers for use in the present invention include, but are not limited to, polyhydric alcohols such as glycerin, polyglycerol, alkyl polyglycosides, diethylene glycol, triethylene glycol, polyethylene glycol, random copolymers of ethylene oxide and propylene oxide, ethylene oxide/propylene oxide block copolymers such as those available from BASF under the Pluronic tradename, propylene glycol, sorbitol, sorbitol esters, butanediol, and their alkoxylated derivatives; monohydric alcohols such as 3-methoxy-3-methyl-1-butanol, alkyl ether ethoxylates, alkyl ester ethoxylates, aryl ether ethoxylates, aryl ester ethoxylates, aralkyl ether ethoxylates or aralkyl ester ethoxylates; urea, pyrrolidone carboxylic acids, pyrrolidone carboxylate salts, triethanol amine, ethanol acetamide, water, certain active agents such as vitamin E (.alpha.-tocopherol) and many common emollients; or any mixture including one or more of the foregoing. Non-polar active agents may be suspended or emulsified in the backing by including a nonionic surfactant having a hydrophilic-lipophilic balance ("HLB") value of at least about 8 as part or all of the plasticizer. Nonionic surfactants having an HLB value of at least about 12 have been shown to have particular general utility. The HLB value indicates the extent to which a given surfactant will behave as an oil-soluble versus a water-soluble type of emulsifier as described in "The Chemistry and Manufacture of Cosmetics," Volume I, Third Edition, Mitchell L. Schlossman, Editor, Allured Publishing Corp., Carol Stream, Ill., 2000. Representative non-ionic surfactants include, without limitation, C8 to C22 alkyl ether ethoxylates, C8 to C22 alkyl ester ethoxylates, sorbitol C8-C22 alkyl esters, sorbitol C8 to C22 alkyl ester ethoxylates, and mixtures including one or more of the foregoing.

The amount of plasticizer present in the backing may vary depending upon, among other things, the polymer used to form the backing and the particular active agent or agents that also may compose the backing. Some backings may be at least about 5% plasticizer, by weight, although some backings may be at least about 3% or at least about 1% plasticizer, by weight. Some backings may be as much as 30% plasticizer, by weight, although other backings may be as much as about 40% or as much as about 50% plasticizer, by weight. Certain backings may include plasticizers in the range of about 5% to about 30% by weight. Such backings generally provide good flexibility without compromising strength.

Water-soluble backings may be prepared by dissolving at least one polymer and at least one plasticizer in water or other appropriate solvent. The solution thus prepared may be cast into a film, then dried. Water-soluble materials such as vitamin C, hydroquinone, and salicylic acid may be dissolved directly into the polymer solution. Water-insoluble materials such as vitamin E, benzoyl peroxide and silicone fluid may be emulsified into the polymer solution with an added surfactant. Alternatively, the active agent may be applied to the backing after it is cast and dried. In this case, the active agent is coated on the surface of the film. If certain characteristics are desired in the final product, additional additives may be combined with the polymer solution in order to impart the desired characteristics to the backing. For example, addition of low levels of silicone fluid or silicone copolyols provides backings with a lubricious feel, addition of a biocide prevents mold or bacterial growth on the backing during storage, and addition of particulate materials, such as the flattening agents used in the paint industry, provides a non-glossy matte finish to the dried backing.

Fabrics useful as backings may be constructed by any known technique for making woven, nonwoven, knitted, or other types of fabrics including open and closed cell foams. Nonwoven techniques include spun bonding, melt blowing, wet laying, hydroentangling (such as with cold water, relatively high salt concentration, or both), thermal bonding, or any combination of the foregoing. Polymeric fibers useful for the manufacture of the fabric are commercially available.

Alternatively, the films or fabrics can be melt processed with the appropriate polymer composition using known techniques. For example, certain plasticized polyvinyl alcohols may be melt processed. Heat-stable active agents may be added directly to the polymer melt. Alternatively, active agents may be coated onto or absorbed into a water-soluble or water-dispersible film or fiber using techniques such as those reported in U.S. Pat. No. 5,688,523. Water-insoluble thermoplastic polymers may be included in the melt to alter the solubility, flexibility, strength, barrier, or other properties of the resulting carrier.

The particular form of the backing and the materials used to prepare the backing may be selected to provide the backing with desired characteristics. For example, a thin, transparent film backing may be desired for applications requiring that the device be substantially unnoticeable in use. A woven or nonwoven fabric backing may be desired for applications in which high porosity is required. A film or higher basis weight nonwoven may be desirable for applications in which a more substantial device is desired.

Pad

Devices for skin contacting applications such as medical adhesive bandages typically include a backing, an absorbent pad, and a PSA to maintain the medical adhesive bandage in place. The devices are typically used to cover cuts, scrapes and other skin conditions but may also be used to cushion and protect an area. The pad is typically absorbent, and can be manufactured from a number of materials including but not limited to, woven or nonwoven cotton, rayon, nonwovens, hydrocolloids, foams, and combinations thereof.

Devices utilizing the water-soluble PSA of the current invention may include a water-soluble non-woven pad such as the polyvinyl alcohol non-woven available from Sheng Hung Industrial Co., Taipei, Taiwan under the E-Tex tradename. The pad may also contain a number of substances, including antimicrobial agents, anesthetics, anti-itch agents, drugs for transdermal drug delivery, chemical indicators to monitor hormones or other substances in a patient, combinations thereof and the like.

Support Layer

A device utilizing the PSA of the present invention may include one or more support layers releasably adhered to the backing, the PSA, or both. The support layer is typically removed from the backing and the PSA at about the time a treatment is initiated. Because the backing and the adhesive of the device may be thin, flexible and conformable, a support layer may be used to provide structural support to the device, thereby making the device easier to handle. A support layer also may cover the PSA until the user is prepared to apply the device to a localized body surface for treatment. In this way, a support layer may protect the PSA layer from contact with surfaces other than the body surface selected for the desired treatment. This improves handling of the device prior to treatment and reduces mess. A second support layer may be adhered to the backing to provide rigidity to the device after removal of the first support layer from the adhesive. This prevents the device from wrinkling or curling up on itself, allowing for smooth, easy placement onto skin. Once the device has been applied to the desired body surface, the second support layer may be removed. One method of producing such a supported device is reported in U.S. Pat. No. 6,169,224.

The material used for the support layer is not limited. Suitable materials for use in the support layer include, but are not limited to, paper, foils, and polymeric films as well as multilayered laminates thereof. The support layer should be easily releasable from the backing or adhesive so that the device may be applied to the body surface receiving treatment. The material for the support layer also may be coated with one or more materials designed to make the support layer easily releasable.

Active Agents

The device of the present invention may be, for example, a patch or other device designed to deliver one or more active agents to a specific, limited body surface. For certain embodiments, a delivered active agent may remain localized at the site of delivery. For other embodiments, an active agent may enter the bloodstream in order to provide a systemic treatment.

A single device of the invention may deliver any number of active agents. More than one active agent may be mixed together so long as each active agent is compatible with each of the other active agents being co-delivered by the same device. Alternatively, an active agent that reacts with a second active agent may be used, configured within the device to be separated from the second active agent by the backing, the adhesive, or both and allowed to react only when the device is activated by moistening. This may be particularly useful for in situ mixing of, for example, baking soda and hydrogen peroxide for oral care.

One or more active agents may be delivered by the device of the present invention by being in association with the backing, the adhesive, or both as the device is applied to the desired body surface. The association between an active agent and the backing or adhesive may include, but is not limited to, as a coating, suspension, emulsion, or solution.

The device of the present invention may be useful for any of a large number and wide variety of treatments, some of which are described below. It should be understood that the description of possible treatments according to the present invention is intended to be exemplary in nature and is not intended to unduly limit the scope of the invention in any way. One skilled in the art will be able to design a device as disclosed herein with properties suitable for use in the described or any other treatments.

The device of the present invention may be used to deliver a broad assortment of active agents to the skin. The claimed device may be flexible and conformable, thereby providing comfortable treatment by the device to various skin contours. For skin treatments, it may be desirable that the device is able to adhere to dry skin, although application to wet or pre-moistened skin is also within the scope of the claimed invention. Adhesion of the device to dry skin allows the device to be used for various applications in which prolonged treatment may be desirable. For example, the device may be used to apply an active agent for an overnight skin treatment. In one embodiment, the device is applied to dry skin, provides prolonged treatment, and then is washed away easily and quickly after treatment is completed. Active agents that may be delivered to the skin in this manner include, but are not limited to, emollients, humectants, conditioners, moisturizers, vitamins, herbal extracts, antioxidants, steroids or other anti-inflammatory agents, vasodilators, exfoliants such as alpha-hydroxy acids or beta-hydroxy acids, growth factors, enzymes, bleaching or coloring agents, antifungal or antimicrobial agents (including antibiotics and antiseptics such as povidone-iodine, chlorhexidine gluconate, triclosan, p-chloro-m-xyenol, fatty acid monoesters of glycerin and propylene glycol, benzoyl peroxide, hydrogen peroxide, silver and silver salts including, but not limited to, silver chloride, silver oxide and silver sulfadiazine, phenols, miconazole, clotrimazole, ketoconazole, econazole, undecylenic acid and the like), emulsifiers, artificial tanning agents, tanning accelerants, skin soothing agents, skin tightening agents, anti-wrinkle agents, skin repair agents, sebum inhibiting agents, sebum stimulators, protease inhibitors, anti-itch ingredients, agents for inhibiting hair growth, agents for accelerating hair growth, skin sensates, anti-acne treatments, depilating agents, astringents, hair removers, or corn, callus or wart removers. Ornamental or decorative designs, colorants, tattoos or glitters also may be applied to skin in this manner. For example, the claimed device may be used to fashion water-removable masks for decorating at least a portion of the skin, including the face.

Alternatively, active agents may be delivered to the skin by at least partially activating the surface area of the device with water or other moisture. In this way, at least some of the adhesive, carrier, or both are dissolved or dispersed. For some treatments, it may be desirable to completely dissolve or disperse the adhesive and backing, thereby providing immediate and complete delivery the active agent. Alternatively, for some treatments it may be desirable to dissolve or disperse only a portion of the backing, adhesive, or both. The remaining backing or adhesive can be rubbed into the skin along with the active agent, thereby serving as a binder providing some degree of substantivity and persistence for the active agent. Active agents that may be delivered to the skin in this manner include, but are not limited to, glitters, fragrances including aromatherapy agents, perfumes, sunscreen agents, insect repellants, deodorants and antiperspirants.

The device also may be used to provide treatment to fingernails or toenails. Decorative colorings or appliques may be delivered to nails with the claimed device in a manner similar to that described above for the similar treatments to skin and hair. Antifungal agents, antimicrobial agents, or other medicinal agents also may be delivered to the nails with the device.

The devices of the invention also may have utility as a wound dressing, first aid bandage, or athletic tape wrap. These medical articles may include active agents such as, without limitation, antimicrobial agents, antibiotics, external analgesics or wound healing agents. These wound dressings may further include water-soluble absorbents.

The device of the present invention also may be used to deliver an active agent that provides a systemic treatment. Delivery of systemic active agents may be through the skin or mucosal tissue. For such a treatment, a device of the present invention carrying the systemically active agent is applied to a localized body surface. The application of the device may be for a prolonged period or, alternatively, the device and active agent may be rubbed into the skin or mucosal tissue to which the device is applied. The active agent is absorbed into the skin or mucosal tissue and passes into the bloodstream. The bloodstream carries the active agent throughout the body, thereby allowing the active agent to provide systemic treatment. Active agents that may be delivered in this manner to provide systemic treatments include, but are not limited to, hormones, vitamins, drugs such as those reported in U.S. Pat. No. 6,019,997, and combinations thereof.

For all treatments, the active agents should be compatible with the backing, adhesive and support layer. The active agents, adhesive and backing should also preferably be selected so that each will remain stable during storage.

EXAMPLES

Objects and advantages of this invention are further illustrated by the following examples, but the particular materials and amounts thereof recited in these examples, as well as other conditions and details, should not be construed to unduly limit this invention.

Test Methods

HLB

The hydrophile-lipophile balance (HLB) was calculated using Davies' HLB method (Proc. 2nd Inter. Congress of Surface Activity, 1426 (1957)).

Tack

Finger tack was assessed and given a rating of 0=tack free, 1=very low tack, 2=low tack, 3=medium tack, 4=good tack, 5=excellent tack.

Water Solubility

A ¾ by 2 inch (1.9 by 5.1 cm) strip was cut along the edge of the coated polyester film. The strip contained both coated film and uncoated film. Holding the uncoated end, the adhesive coated portion was immersed and withdrawn from room temperature water in a beaker 20 times over the course of 20 seconds. The wet film was laid onto a glass slide, adhesive side up, and a finger was gently run down its length. An adhesive which was not readily water soluble produced a cohesive film or a gummy, high viscosity feel. The absence of a cohesive film or a slimy, low viscosity feel was deemed to be from adhesive coatings which are readily water soluble.

% Moisture Uptake

The moisture uptake and cohesiveness of the polymer/plasticizer blend was assessed by spreading a portion of the solution (containing 0.3-0.6 g solids) across the bottom of a pre-weighed (A=empty weight) 6 cm diameter circular aluminum tin. After drying overnight in a forced air oven at 80° C., the tin was reweighed (B=tin plus dry adhesive), then placed in a chamber at 75% RH and 40° C. for 2 days. Shortly after being removed, the tin was weighed a final time (C=tin plus hydrated adhesive) and then tack was assessed for the hydrated adhesive. Any cohesive failure (adhesive transfer to the finger) was noted and % moisture uptake was calculated using the formula $100 \times (C-B)/(B-A)$.

Sample Preparation

Examples were prepared by combining the polymer solution as received with a similar amount of plasticizer based on solids. Polymers which were provided as 100% solid powders were first dissolved in ethanol to 25% solids, and then combined 4:1 with the plasticizer to yield the 1:1 blend based on solids. After mixing to homogeneity, a portion was coated at 1 mil (0.001 inch, 25 micron) dry coating thickness onto 1.2 mil (30 micron) polyester film. The film was dried for 8 minutes at 80° C. then cooled to room temperature prior to testing. The polymers and plasticizers utilized in the adhesive compositions are shown in Tables 1 and 2, respectively. Test results are shown in Table 3.

TABLE 1

| Code | Polymer | INCI[a] Name | Manufacturer |
| --- | --- | --- | --- |
| PO-1 | Advantage ™ HC-37 | Vinyl caprolactam/vinylpyrrolidone/dimethylaminoethyl methacrylate copolymer | ISP corporation, Wayne, NJ |
| PO-2 | Advantage ™ LC-A | Vinyl caprolactam/vinylpyrrolidone/dimethylaminoethyl methacrylate copolymer | ISP corporation, Wayne, NJ |
| PO-3 | Advantage ™ S | Vinyl caprolactam/vinylpyrrolidone/dimethylaminoethyl methacrylate copolymer | ISP corporation, Wayne, NJ |
| PO-4 | Aquaflex ™ SF-40 | Vinylpyrrolidone/vinyl caprolactam/DMAPA acrylates copolymer | ISP corporation, Wayne, NJ |
| PO-5 | PVA/VA E335 | 30/70 N-vinyl pyrrolidone/vinyl acetate copolymer | ISP corporation, Wayne, NJ |
| PO-6 | Gaffix ™ VC 713 | Vinyl Caprolactam/vinylpyrrolidone/dimethylaminoethyl methacrylate copolymer | ISP corporation, Wayne, NJ |
| PO-7 | Luviskol ® Plus | Polyvinylcaprolactam | BASF corporation, Ludwigshafen, Germany |

TABLE 1-continued

| Code | Polymer | INCI[a] Name | Manufacturer |
|---|---|---|---|
| PO-8 | PVA/VA I535 | 50/50 N-vinyl pyrrolidone/vinyl acetate copolymer in isopropanol | ISP corporation, Wayne, NJ |
| PO-9 | PVA/VA E535 | 50/50 N-vinyl pyrrolidone/vinyl acetate copolymer in ethanol | ISP corporation, Wayne, NJ |
| PO-10 | Luviskol ® K30 | Polyvinylpyrrolidone | BASF corporation, Ludwigshafen, Germany |

[a]International Nomenclature of Cosmetic Ingredients

TABLE 2

| Code | Plasticizer | INCI[a] Name | Manufacturer |
|---|---|---|---|
| PL-1 | Polyglycol P425 | PPG-12 | Dow Chemical Midland, MI |
| PL-2 | Polymeg 650 | Polytetramethylene Glycol | LyondellBasell Industries, the Netherlands |
| PL-3 | Brij L-4 | Laureth 4 (2-dodecoxyethanol) | Croda, Edison, NJ |
| PL-4 | Sensiva ® SC50 | Ethylhexylglycerin | Schulke and Myer, Norderstedt, Germany |
| PL-5 | Capmul ® PG-8 | Propylene glycol monocaprylate | Abitec, Janesville, WI |
| PL-6 | Symdiol ® 68 | 1,2-hexanediol and 1,2-octanediol | Symrise, Holzminden, Germany |
| PL-7 | CAPA 2054 | Polycaprolactone | Perstop Polyols, Toledo, OH |
| PL-8 | TBC NF | Tributyl citrate | Morflex Inc. Greensboro, NC |
| PL-9 | Lexgard ® GMCY | Glyceryl Caprylate | Inolex, Philadelphia, PA |
| PL-10 | Glycerin | Glycerin | EM Industries, Gibstown, NJ |
| PL-11 | Carbowax ® PEG 400 | PEG-8 | Dow Chemical, Midland, MI |
| PL-12 | Century ® 1107 | Isostearic acid | Arizona Chemical, Jacksonville, FL |

[a]International Nomenclature of Cosmetic Ingredients

TABLE 3

| Example | Polymer | Plasticizer | HLB | Tack | Water Soluble | % Moisture Uptake |
|---|---|---|---|---|---|---|
| 1 | PO-1 | 100 phr PL-1 | 8.6 | 4.5 | Yes | 12.9 |
| 2 | PO-1 | 100 phr PL-2 | 4.2 | 3 | Yes | 10.2 |
| 3 | PO-2 | 100 phr PL-1 | 8.6 | 4 | Yes | 14.6 |
| 4 | PO-2 | 100 phr PL-2 | 4.2 | 4.5 | Yes | 13.2 |
| 5 | PO-3 | 90 phr PL-1 | 8.6 | 3 | Yes | 11.0 |
| 6 | PO-3 | 100 phr PL-1 | 8.6 | 4 | Yes | 10.9 |
| 7 | PO-3 | 110 phr PL-1 | 8.6 | 4 | Yes | 10.2 |
| 8 | PO-3 | 80 phr PL-1/30 phr PL-3 | 7.5 | 4.5 | Yes | 7.0 |
| 9 | PO-3 | 100 phr PL-2 | 4.2 | 2.5 | Yes | 6.6 |
| 10 | PO-4 | 100 phr PL-1 | 8.6 | 5 | Yes | 12.6 |
| 11 | PO-4 | 100 phr PL-2 | 4.2 | 4 | Yes | 8.0 |
| 12 | PO-5 | 70 phr PL-1 | 8.6 | 4.5 | Yes | 6.7 |
| 13 | PO-5 | 66 phr PL-2 | 4.2 | 1 | Yes | 7.2 |
| 14 | PO-6 | 100 phr PL-1 | 8.6 | 4.5 | Yes | 12.5 |
| 15 | PO-6 | 100 phr PL-2 | 4.2 | 3.5 | Yes | 10.0 |
| 16 | PO-7 | 100 phr PL-1 | 8.6 | 4 | Yes | 11.1 |
| 17 | PO-7 | 100 phr PL-2 | 4.2 | 3 | Yes | 7.1 |
| 18 | PO-8 | 80 phr PL-4 | 6.9 | 5 | Yes | — [a] |
| 19 | PO-8 | 50 phr PL-5 | 6.6 | 3.5 | Yes | — |
| 20 | PO-5 | 60 phr PL-5 | 6.6 | 5 | Yes | — |
| 21 | PO-8 | 50 phr PL-6 | 7.5 | 4 | Yes | — |
| 22 | PO-5 | 65 phr PL-6 | 7.5 | 4 | Yes | — |
| 23 | PO-9 | 100 phr PL-7 | 10.0 | 4.5 | Yes | — |
| 24 | PO-9 | 66 phr PL-8 | 9.5 | 2.5 | Yes | — |
| 25 | PO-9 | 100 phr PL-8 | 9.5 | 5 | Yes | — |
| 26 | PO-5 | 100 phr PL-8 | 9.5 | 5 | Yes | — |
| 27 | PO-9 | 66 phr PL-9 | 6.3 | 8.5 | Yes | — |
| Comp. 1 [b] | PO-10 | 40 phr PL-10 | 11.3 | 1.5 | Yes | 20.0 - honey like |
| Comp. 2 [c] | PO-10 | 50 phr PL-11 | 12.5 | 3 | Yes | 23.5 - honey like |
| Comp. 3 [d] | PO-8 | 100 phr PL-12 | 1.0 | 4.5 | No | 5.0 |
| Comp. 4 [d] | PO-5 | 100 phr PL-12 | 1.0 | 5 | No | 3.1 |

[a] — = Not Tested
[b] Reproduction of Example 1 from WO 95/05416
[c] Reproduction of Example 17 from U.S. patent application Pub. No. 2002/0187181
[d] Reproduction of Example 3 from U.S. Pat. No. 4,331,576 - monomer ratio of VP/VOAc copolymer not specified The complete disclosures of the publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

I claim:

1. An adhesive comprising a homogeneous blend comprising:
   (a) a polymer selected from the group consisting of N-vinyl caprolactam homopolymers, N-vinyl pyrrolidone copolymers, and mixtures thereof, the N-vinylpyrrolidone copolymers comprising about 60% or less by weight N-vinyl pyrrolidone; and
   (b) a non-volatile plasticizer comprising a monohydric alcohol having hydrophilic-lipophilic balance of about 4 to about 9;
   wherein the plasticizer comprises from about 33% to about 80% by weight of the adhesive such that the adhesive is pressure sensitive, water-soluble, and increases in weight less than about 15% after two days at 75% relative humidity and 40° C.

2. The pressure sensitive adhesive of claim 1 wherein the polymer comprises from about 35% to about 75% by weight of the pressure sensitive adhesive.

3. The pressure sensitive adhesive of claim 1 wherein the polymer is an N-vinyl caprolactam homopolymers.

4. The pressure sensitive adhesive of claim 1 wherein the polymer is an N-vinyl pyrrolidone copolymer.

5. The pressure sensitive adhesive of claim 4, wherein the polymer is selected from the group consisting of N-vinyl caprolactam/N-vinyl pyrrolidone copolymers and vinyl acetate/N-vinyl pyrrolidone copolymers, the vinyl acetate/N-vinyl pyrrolidone copolymers comprising from about 20% to about 60% by weight N-vinyl pyrrolidone.

6. The pressure sensitive adhesive of claim 5, wherein the polymer is a copolymer of N-vinyl pyrrolidone and vinyl acetate comprising from about 30% to about 50% by weight N-vinyl pyrrolidone.

7. The pressure sensitive adhesive of claim 1 wherein the N-vinylpyrrolidone copolymers comprise about 30% or less by weight N-vinyl pyrrolidone.

8. The pressure sensitive adhesive of claim 1 wherein the polymer further comprises a comonomer in an amount up to about 10% by weight, the comonomer having no carboxylic acid functionality or tetraalkyl ammonium functionality.

9. The pressure sensitive adhesive of claim 1 wherein the plasticizer has a vapor pressure below about 0.1 mm Hg at 20° C.

10. The pressure sensitive adhesive of claim 1 wherein the plasticizer is selected from the group consisting of polyether glycols having a carbon to oxygen mole ratio greater than about 2.5:1, polyester polyols, C5-C10 alkyl diols, C4-C10 carboxylate monoesters of propylene glycol, C4-C10 carboxylate mono- and diesters of glycerin, C4-C10 alkyl monoethers of propylene glycol, C4-C10 alkyl mono- and diethers of glycerin, C4-C10 alkyl esters of lactic acid, C2-C4 triesters of citric acid, and mixtures thereof.

11. An adhesive comprising a homogeneous blend comprising:
   (a) a polymer selected from the group consisting of N-vinyl caprolactam homopolymers, N-vinyl pyrrolidone copolymers, and mixtures thereof, the N-vinylpyrrolidone copolymers comprising about 60% or less by weight N-vinyl pyrrolidone; and
   (b) a non-volatile plasticizer comprising a monohydric alcohol having hydrophilic-lipophilic balance of about 4 to about 9; selected from the group consisting of C4-C10 monoesters and ethers of propylene glycol, C4-C10 diesters and ethers of glycerin, C4-C10 alkyl esters of lactic acid, C2-C4 triesters of citric acid, and mixtures thereof, wherein the plasticizer comprises from about 10% to about 80% by weight of the adhesive, such that the adhesive is pressure sensitive, water-soluble, and increases in weight less than about 15% after two days at 75% relative humidity and 40° C.

12. The pressure sensitive adhesive of claim 11, wherein the polymer comprises from about 35% to about 75% by weight of the pressure sensitive adhesive.

13. The pressure sensitive adhesive of claim 11, wherein the polymer is an N-vinyl pyrrolidone copolymer.

14. The pressure sensitive adhesive of claim 11, wherein the pressure sensitive adhesive increases in weight less than about 10% after two days at 75% relative humidity and 40° C.

15. A device for skin contacting applications comprising a flexible backing and the pressure sensitive adhesive of claim 1 on at least a portion of the skin facing side of the flexible backing.

16. The device of claim 15 wherein the backing is water-soluble.

17. A device for skin contacting applications comprising a flexible backing and the pressure sensitive adhesive of claim 11 on at least a portion of the skin facing side of the flexible backing, wherein the backing is water-soluble.

18. A method for removing a pressure sensitive adhesive from skin, the method comprising:
   providing a device comprising a flexible backing and the pressure sensitive adhesive disposed on a least a portion of one side of the flexible backing, wherein the pressure sensitive adhesive comprises a homogeneous blend including (a) a polymer selected from the group consisting of N-vinyl caprolactam homopolymers, N-vinyl pyrrolidone copolymers, and mixtures thereof, the N-vinylpyrrolidone copolymers comprising about 60% or less by weight N-vinyl pyrrolidone; and (b) a non-volatile plasticizer comprising a monohydric alcohol having hydrophilic-lipophilic balance of about 4 to about 9, wherein the plasticizer comprises from about 10% to about 80% by weight of the adhesive and the adhesive is pressure sensitive and water-soluble, and wherein the pressure sensitive adhesive increases in weight less than about 15% after two days at 75% relative humidity and 40° C.;
   dissolving the pressure sensitive adhesive in water;
   and removing the backing.

19. The method of claim 18, wherein the backing is water soluble, and wherein removing the backing comprises dissolving the backing in water.

* * * * *